US005405943A

United States Patent [19]
Comings

[11] Patent Number: 5,405,943
[45] Date of Patent: Apr. 11, 1995

[54] TOURETTE SYNDROM, AUTISM AND ASSOCIATED BEHAVIORS

[75] Inventor: David E. Comings, Duarte, Calif.

[73] Assignee: City of Hope, Duarte, Calif.

[21] Appl. No.: 562,596

[22] Filed: Aug. 3, 1990

Related U.S. Application Data

[63] Continuation-in-part of Ser. No. 125,577, Nov. 25, 1987, abandoned, and a continuation-in-part of Ser. No. 271,653, Nov. 16, 1988, abandoned, and a continuation-in-part of Ser. No. 410,831, Sep. 22, 1989, abandoned.

[51] Int. Cl.⁶ .................... C07H 21/02; C07H 21/04; C12Q 1/68; C12N 15/00
[52] U.S. Cl. ........................ 536/23.5; 435/6; 935/77; 935/78
[58] Field of Search ............ 435/6; 536/27, 23.5; 935/77, 78

[56] References Cited

PUBLICATIONS

Fritsch et al., Cell, vol. 19, Apr. 1980 pp. 959–972.
Mangoni, Adv. in Biochem. Psychoprarm. vol. 11, 1974, pp. 293–298.
White et al, Principles of Biochemistry, McGraw–Hill, p. 750.
Matsubara et al, Proc. Natl. Acad. Sci, vol. 83, Sep. 1986, pp. 6543–6547.
Schmid et al, EMBO J, vol. 1, No. 10, 1982, pp. 1287–1293.

*Primary Examiner*—Mindy B. Fleisher
*Attorney, Agent, or Firm*—Edward S. Irons

[57] ABSTRACT

The human tryptophan oxygenase gene sequence and chromosomal location are described. Procedures for the diagnosis of genetic Tourette syndrome and many psychiatric and behavioral disorders by genetic tests to identify deletions or defective alleles in the human tryptophan oxygenase (TO) gene and cDNA probes for use in such tests are also described.

3 Claims, 12 Drawing Sheets

Sequence: Human TDO2

```
  1 acctccgtgc ttctcagaca gtgccttttc
    tggaggcacg aagagtctgt cacggaaaag met ser gly cys pro phe leu gly asn
 31 acc     ATG AGT GGG TGC CCA TTT TTA GGA AAC
    tgg     TAC TCA CCC ACG GGT AAA AAT CCT TTG asn phe gly tyr thr phe lys lys leu pro
 61     AAC TTT GGA TAT ACT TTT AAA AAA CTC CCC
        TTG AAA CCT ATA TGA AAA TTT TTT GAG GGG val glu gly ser glu glu asp lys ser gln
 91     GTA GAA GGC AGC GAA GAA GAC AAA TCA CAA
        CAT CTT CCG TCG CTT CTT CTG TTT AGT GTT thr gly val asn arg ala ser lys gly gly
121     ACT GGT GTG AAT AGA GCC AGC AAA GGA GGT
        TGA CCA CAC TTA TCT CGG TCG TTT CCT CCA leu ile tyr gly asn tyr leu his leu glu
151     CTT ATC TAT GGG AAC TAC CTG CAT TTG GAA
        GAA TAG ATA CCC TTG ATG GAC GTA AAC CTT lys val leu asn ala gln glu leu gln ser
181     AAA GTT TTG AAT GCA CAA GAA CTG CAA AGT
        TTT CAA AAC TTA CGT GTT CTT GAC GTT TCA glu thr lys gly asn lys ile his asp glu
211     GAA ACA AAA GGA AAT AAA ATC CAT GAT GAA
        CTT TGT TTT CCT TTA TTT TAG GTA CTA CTT his leu phe ile ile thr his gln ala tyr
241     CAT CTT TTT ATC ATA ACT CAT CAA GCT TAT
        GTA GAA AAA TAG TAT TGA GTA GTT CGA ATA glu leu trp phe lys gln ile leu trp glu
271     GAA CTC TGG TTT AAG CAA ATC CTC TGG GAG
        CTT GAG ACC AAA TTC GTT TAG GAG ACC CTC leu asp ser val arg glu ile phe gln asn
301     TTG GAT TCT GTT CGA GAG ATC TTT CAG AAT
        AAC CTA AGA CAA GCT CTC TAG AAA GTC TTA gly his val arg asp glu arg asn met leu
331     GGC CAT GTC AGA GAT GAA AGG AAC ATG CTT
        CCG GTA CAG TCT CTA CTT TCC TTG TAC GAA lys val val ser arg met his arg val ser
361     AAG GTT GTT TCT CGG ATG CAC CGA GTG TCA
        TTC CAA CAA AGA GCC TAC GTG GCT CAC AGT val ile leu lys leu leu val gln gln phe
391     GTG ATC CTG AAA CTG CTG GTG CAG CAG TTT
        CAC TAG GAC TTT GAC GAC CAC GTC GTC AAA ser ile leu glu thr met thr ala leu asp
421     TCC ATT CTG GAG ACG ATG ACA GCC TTG GAC
        AGG TAA GAC CTC TGC TAC TGT CGG AAC CTG
```

FIG.5-1

```
        phe  asn  asp  phe  arg  glu  tyr  leu  ser  pro
451     TTC  AAT  GAC  TTC  AGA  GAG  TAC  TTA  TCT  CCA
        AAG  TTA  CTG  AAG  TCT  CTC  ATG  AAT  AGA  GGT ala  ser  gly  phe  gln  ser  leu  gln  phe  arg
481     GCA  TCA  GGC  TTC  CAG  AGT  TTG  CAA  TTC  CGA
        CGT  AGT  CCG  AAG  GTC  TCA  AAC  GTT  AAG  GCT leu  leu  glu  asn  lys  ile  gly  val  leu  gln
511     CTA  TTA  GAA  AAC  AAG  ATA  GGT  GTT  CTT  CAG
        GAT  AAT  CTT  TTG  TTC  TAT  CCA  CAA  GAA  GTC asn  met  arg  val  pro  tyr  asn  arg  arg  his
541     AAC  ATG  AGA  GTC  CCT  TAT  AAC  AGA  AGA  CAT
        TTG  TAC  TCT  CAG  GGA  ATA  TTG  TCT  TCT  GTA tyr  arg  asp  asn  phe  lys  gly  glu  glu  asn
571     TAT  CGT  GAT  AAC  TTC  AAA  GGA  GAA  GAA  AAT
        ATA  GCA  CTA  TTG  AAG  TTT  CCT  CTT  CTT  TTA gTu  leu  leu  leu  lys  ser  glu  gln  glu  lys
601     GAA  CTG  CTA  CTT  AAA  TCT  GAG  CAG  GAA  AAG
        CTT  GAC  GAT  GAA  TTT  AGA  CTC  GTC  CTT  TTC thr  leu  leu  glu  leu  val  glu  ala  trp  leu
631     ACA  CTT  CTG  GAA  TTA  GTG  GAG  GCA  TGG  CTG
        TGT  GAA  GAC  CTT  AAT  CAC  CTC  CGT  ACC  GAC glu  arg  thr  pro  gly  leu  glu  pro  his  gly
661     GAA  AGA  ACT  CCA  GGT  TTA  GAG  CCA  CAT  GGA
        CTT  TCT  TGA  GGT  CCA  AAT  CTC  GGT  GTA  CCT phe  asn  phe  trp  gly  lys  leu  glu  lys  lys
691     TTT  AAC  TTC  TGG  GGA  AAG  CTT  GAA  AAA  AAA
        AAA  TTG  AAG  ACC  CCT  TTC  GAA  CTT  TTT  TTT tyr  his  gln  arg  pro  gly  arg  gly  ile
721     TAT  CAC  CAG  AGG  CCT  GGA  AGA  GGA  ATT  C
        ATA  GTG  GTC  TCC  GGA  CCT  TCT  CCT  TAA  G
```

FIG.5-2

```
  1 acctccgtgc ttctcagaca gtgccttttc 1 met ser gly cys pro phe leu gly asn
 31 acc ATG AGT GGG TGC CCA TTT TTA GGA AAC 10 asn phe gly tyr thr phe lys lys leu pro
 61 AAC TTT GGA TAT ACT TTT AAA AAA CTC CCC 20 val glu gly ser glu glu asp lys ser gln
 91 GTA GAA GGC AGC GAA GAA GAC AAA TCA CAA 30 thr gly val asn arg ala ser lys gly gly
121 ACT GGT GTG AAT AGA GCC AGC AAA GGA GGT 40 leu ile tyr gly asn tyr leu his leu glu
151 CTT ATC TAT GGG AAC TAC CTG CAT TTG GAA 50 lys val leu asn ala gln glu leu gln ser
181 AAA GTT TTG AAT GCA CAA GAA CTG CAA AGT 60 glu thr lys gly asn lys ile his asp glu
211 GAA ACA AAA GGA AAT AAA ATC CAT GAT GAA 70 his leu phe ile ile thr his gln ala tyr
241 CAT CTT TTT ATC ATA ACT CAT CAA GCT TAT 80 glu leu trp phe lys gln ile leu trp glu
271 GAA CTC TGG TTT AAG CAA ATC CTC TGG GAG 90 leu asp ser val arg glu ile phe gln asn
301 TTG GAT TCT GTT CGA GAG ATC TTT CAG AAT 100 gly his val arg asp glu arg asn met leu
331 GGC CAT GTC AGA GAT GAA AGG AAC ATG CTT 110 lys val val ser arg met his arg val ser
361 AAG GTT GTT TCT CGG ATG CAC CGA GTG TCA 120 val ile leu lys leu leu val gln gln phe
391 GTG ATC CTG AAA CTG CTG GTG CAG CAG TTT 130 ser ile leu glu thr met thr ala leu asp
421 TCC ATT CTG GAG ACG ATG ACA GCC TTG GAC 140 phe asn asp phe arg glu tyr leu ser pro
451 TTC AAT GAC TTC AGA GAG TAC TTA TCT CCA 150 ala ser gly phe gln ser leu gln phe arg
481 GCA TCA GGC TTC CAG AGT TTG CAA TTC CGA 160 leu leu glu asn lys ile gly val leu gln
511 CTA TTA GAA AAC AAG ATA GGT GTT CTT CAG 170 asn met arg val pro tyr asn arg arg his
541 AAC ATG AGA GTC CCT TAT AAC AGA AGA CAT 180 tyr arg asp asn phe lys gly glu glu asn
571 TAT CGT GAT AAC TTC AAA GGA GAA GAA AAT 190 glu leu leu leu lys ser glu gln glu lys
```

FIG.5A-1

```
601        GAA CTG CTA CTT AAA TCT GAG CAG GAA AAG
    200    thr leu leu glu leu val glu ala trp leu
    631    ACA CTT CTG GAA TTA GTG GAG GCA TGG CTG
    210    glu arg thr pro gly leu glu pro his gly
    661    GAA AGA ACT CCA GGT TTA GAG CCA CAT GGA
    220    phe asn phe trp gly lys leu glu lys lys
    691    TTT AAC TTC TGG GGA AAG CTT GAA AAA AAA
    230    tyr his gln arg pro gly arg         - 236
    721    TAT CAC CAG AGG CCT GGA AGA     (G) - 741
    237    ile arg ile gln ala lys glu glu ser glu
    742    ATA AGG ATT CAG GCT AAA GAA GAG TCT GAA
    247    glu lys glu glu gln val ala glu phe gln
    772    GAA AAA GAG GAA CAG GTG GCT GAA TTT CAG
    257    lys gln lys glu val leu leu ser leu phe
    802    AAG CAA AAA GAG GTG CTA CTG TCC TTA TTT
    267    asp glu lys arg his glu his leu leu ser
    832    GAT GAG AAA CGT CAT GAA CAT CTC CTT AGT
    277    lys gly glu arg arg leu ser tyr arg ala
    862    AAA GGT GAA AGA CGG CTG TCA TAC AGA GCA
    287    leu gln gly ala leu met ile tyr phe tyr
    892    CTT CAG GGA GCA TTG ATG ATA TAT TTT TAC
    287    arg glu glu pro arg phe gln val pro phe
    922    AGG GAA GAG CCT AGG TTC CAG GTG CCT TTC
    297    ser leu ala asp phe ser tyr gly his arg
    952    AGT TTA GCT GAC TTC TCT TAT GGA CAT AGA
    307    phe thr asp asp gln trp arg ile TER pro
    982    TTC ACT GAT GAC CAA TGG AGG ATA TAA CCA
    317    cys gly met val his arg ile val gly ser
    1022   TGT GGC ATG GTG CAC AGA ATC GTG GGC AGC
    327    lys ala gly thr gly gly ser ser gly tyr
    1052   AAA GCT GGC ACC GGT GGT TCC TCA GGC TAT
    337    his tyr leu arg ser thr val ser asp arg
    1082   CAC TAC CTG CGA TCA ACT GTG AGT GAT AGG
    347    tyr lys val phe val asp leu phe asn leu
    1112   TAC AAG GTA TTT GTA GAT TTA TTT AAT CTT
```

FIG.5A-2

```
 357 ser thr tyr leu ile pro arg his trp ile
1142 TCA ACA TAC CTG ATT CCC CGA CAC TGG ATA 367 pro lys met asn pro thr ile his lys phe
1172 CCG AAG ATG AAC CCA ACC ATT CAC AAA TTT 377 leu tyr thr ala glu tyr cys asp arg leu
1202 CTA TAT ACA GCA GAA TAC TGT GAT AGA TTA 387 lys ser ser ala lys ser met lys asn thr
1232 AAA TCG TCT GCA AAA TCT ATG AAG AAT ACT 397 gly phe thr ala tyr phe leu phe ser met
1262 GGT TTC ACA GCC TAT TTT TTA TTT TCT ATG 407 asp phe his lys tyr ser leu asn ile cys
1292 GAT TTT CAT AAA TAC AGT TTG AAT ATA TGT 417 met his ile leu phe ser thr thr met leu
1322 ATG CAT ATA TTG TTC AGC ACC ACG ATG CTC 427 TER
1352 tga ttt aat tct aga aac aat ttg att acc
1382 tct tgt ttg tga caa gac taa gca tta aga
1412 tga gaa aga ata cat tta aat agt aac att
1442 gta cat agg gtg ttt tcc tat taa aaa tca
1472 gtt tcc cct gag act taa tgt aac cac tta
1502 atg taa tca cta tct cat tgt ttc atc ttt
1532 ata aac ttg taa act cat cta ttt caa ata
1562 ttt tat gca gta cat tat att att ctg tac
1592 aaa ggc ttt caa aca aaa ttt tta aaa taa
1622 taa agt att aat ctt tca aaa aaa aaa aaa
1652 aaa aaa
```

FIG.5A-3

Sequence: Rat TO cDNA   565   nucleotides

```
  1 AACAGGGTAG GATATCTTTG AAAAACTTAT CTATGGAAGA
 41 CAATGAAGAA GACGGAGCTC AAACTGGTGT AAACAGAGCC
 81 AGCAAAGGAG GACTTATCTA TGGGGACTAC TTGCAGTTGG
121 AGAAGATTTT GAATGCACAA GAACTTCAAA GTGAAATCAA
161 AGGGAATAAA ATCCACGACG AGCACCTCTT TATTATAACT
201 CACCAAGCTT ATGAACTTTT GGTTTAAACA AATTCTCTGG
241 GAACTTTGAT TCTGTTCGTG AGATTTTTCA AAATGGCCAA
281 TGTCAGGGAT GAGAGGAACA TGCTCAAGGT GATGACNNGG
321 ATGCACCGTG TGGTGGTCAT CTTCAAGCTC CTGGTACAGC
361 AGTTCTCGGT TCTGGAAACA ATGACTGCCT TGGACTTCAA
401 TGACTTCAGA GAGTACCTGT CTCCAGCATC AGGCTTCCAG
441 AGTCTTCAGT TCCGGCTGCT AGAAAATAAG ATAGGTGTTC
481 TTCAGAGCTT GAGAGTCCCT TACAACAGGA AACACTATCG
521 TGATAACTTT GAAGGAGACT ACAATGAGCT GCTCCCCCCC
561 CCCCC
```

FIG.6

Sequence: D/HTOCOMPLETE    747   nucleotides

```
  1 ACCTCCGTGC TTCTCAGACA GTGCCTTTTC ACCATGAGTG

Rat TO cDNA  AAC AGGGTAGGAT AT CTTTGAA
 41 GGTGCCCATT TTTAGGAAAC AACTTTGGAT ATACTTTTAA

AAACTTATCT ATGGAAGACA ATGAAGAAGA CGGAGCTCAA
 81 AAAACTCCCC GTAGAAGGCA GTGAAGAAGA CAAATCACAA

ACTGGTGTAA ACAGAGCCAG CAAAGGAGGA CTTATCTATG
121 ACTGGTGTGA ATAGAGCCAG CAAAGGAGGT CTTATTTATG

GGGACTACTT GCAGTTGGAG AAGATTTTGA ATGCACAAGA
161 GGAACTACCT GCATTTGGAA AAAGTTTTGA ATGCACAAGA

ACTTCAAAGT GAAATCAAAGGG AATAAAATC CACGACGAGC
201 ACTGCAAAGT GAA        CAAAAGGAAATAAAATC CATGATGAAC

ACCTCTTTATTATAACTCACC AAG CTTATG AATCTTTGGTT
241 ATCTTTTTTC ATAACTCATC AAGGCTTATG AA CTCTGGTT

TAAACAAATT CTCTGGGAACTTTGATTCTGT TCGTGAGATT
281 TAAGCAAATC CTCTGGGAGT TGGATTCTGT TCGAGAGATC

TTTCAAAATG GCCAATGTCAG GGATGAGAGG AACATGCTCA
321 TTTCAGAATG GCCA TGTCAG AGATGAAAGG AACATGCTTA

AGGTGATGAC TCGGATGCAC CGTGTGGTGG TCATCTTCAA
361 AGGTTGTTTC TCGGATGCAC CGAGTGTCAG TGATCCTGAA

GCTCCTGGTA CAGCAGTTCT CGGTTCTGGA AACAATGACT
401 ACTGCTGGTG CAGCAGTTTT CCATTCTGGA GACGATGACA

GCCTTGGACT TCAATGACTT CAGAGAGTAC CTGTCTCCAG
441 GCCTTGGACT TCAATGACTT CAGAGAGTAC TTATCTCCAG

CATCAGGCTT CCAGAGTCTT CAGTTCCGGC TGCTAGAAAA
481 CATCAGGCTT CCAGAGTTTG CAATTCCGAC TATTAGAAAA

TAAGATAGGT GTTCTTCAGA GCTTGAGAGT CCCTTACAAC
521 CAAGATAGGT GTTCTTCAGA ACATGAGAGT CCCTTATAAC

AGGAAACACT ATCGTGATAA CTTTGAAGGA GACTACAATG
561 AGAAGACATT ATCGTGATAA CTTCAAAGGA GAAGAAAATG

AGCTGCTCC   Rat TO cDNA 551
601 AACTGCTACT TAAATCTGAG GCAGGAAAAG ACACTTCTGG

641 AATTAGTGGA GGCATGGCTG GAAAGAACTC CAGGTTTAGA

681 GCCACATGGA TTTAACTTCT GGGGAAAGCT TGAAAAAAAT

721 ATCACCAGAG GCCTGGAAGA GGAATTC
```

| Hybrid Cells | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y | A.R. |
|---|---|---|---|---|---|---|---|---|---|---|---|---|---|---|---|---|---|---|---|---|---|---|---|---|---|
| 84-2 | + | 10 | + | + | + | + | + | + | + | + | + | + | + | + | + | + | + | + | + | + | + | + | | | + |
| 84-3 | + | + | + | + | + | + | + | + | + | + | + | + | + | + | + | + | + | + | + | + | + | + | | | + |
| 84-7 | | | + | + | + | + | + | + | + | + | + | + | + | + | + | + | + | + | + | + | + | + | | | + |
| 84-20 | | 20 | + | + | + | + | + | + | + | + | + | + | + | + | + | + | + | + | + | + | + | + | | | + |
| 84-21 | | | + | # | 27 | + | + | + | + | + | 6 | + | + | + | 10 | + | + | + | + | + | + | + | 17 | | + |
| 84-25 | | | + | + | + | + | + | + | 9 | + | + | + | + | + | 17 | + | + | + | + | + | + | + | | 9 | + |
| 84-26 | + | | + | 27 | + | + | + | + | 14 | + | + | + | + | + | 4 | + | + | 18 | + | 30 | + | + | + | | ! |
| 84-30 | | | + | 23 | + | + | + | + | 15 | + | + | 15 | + | + | 2 | + | + | + | + | 5 | + | + | | | ! |
| 84-34 | | | + | + | + | + | + | + | + | + | + | + | + | + | + | + | + | + | + | + | + | + | | | + |
| 84-35 | + | | + | + | + | + | + | + | + | + | + | + | + | + | + | + | 17 | + | + | + | + | + | | | + |
| 84-38 | | | + | + | + | + | + | + | + | + | + | + | + | + | + | + | + | + | + | 3 | + | + | | + | + |
| 116-5 | + | + | + | + | + | + | + | + | • | + | + | + | + | + | + | + | + | + | + | + | + | + | • | | ! |
| 84-27 | + | + | | + | | | + | + | | | | 3 | 11 | + | + | + | + | 3 | + | + | + | + | | | ! |
| 84-39 | | + | + | | | | | | | | | | | | | | | | | | | | | | ! |
| 84-5 | + | + | 30 | | | | | | | | | | | | | | | | | | | | | | ! |
| 11-4 | + | + | | 0 | | | | | •• | | | | | | | | | | | | | | •• | + | ! |
| # discrepencies | 7 | 10 | 6 | 0 | 7 | 4 | 4 | 5 | 13 | 4 | 8 | 3 | 8 | 8 | 6 | 4 | 5 | 3 | 7 | 3 | 8 | 6 | 11 | 11 | |

Human Chromosomes In Hybrid Cells discrepencies

+ = the chromosome is present in >30% of analysed cells
N = actual % of chromosome in analysed cells when <30%
• = t(X:10) xqter->xpter::10qil-> 10qter in all cells
•• = t(X:9) 9pter->q34::xql3 -> xqter in all cells
# = chromosome 4 material present by other probing

TOURETTE SYNDROM, AUTISM AND ASSOCIATED BEHAVIORS

This application is a continuation-in-part of each of application Ser. No. 125,577, filed Nov. 25, 1987, abandoned, application Ser. No. 271,653, filed Nov. 16, 1988, abandoned, and application Ser. No. 410,831, filed Sep. 22, 1989, abandoned. Each of these applications is incorporated into this application by reference.

BACKGROUND

Tourette syndrome (TS) is a common, hereditary, neuro-behavioral disorder characterized by motor and vocal tics. Autism is a trait of three sets of symptoms: (1) a profound failure to develop social relationships; (2) defective speech and language; and (3) ritualistic or compulsive behavior.

The symptoms of TS and its related disorders fit a model in which the frontal lobe and limbic system in the brain are disinhibited by a relative deficiency in brain serotonin and tryptophan.

Like TS, autism and MR are neurological disorders. The areas of the brain involved in autism and MR, the frontal lobe and limbic system, are often the same as those involved in TS. Unlike TS where both brain serotonin and tryptophan levels tend to be low, in autism and MR each is often significantly elevated.

Tryptophan-2,3 dioxygenase (tryptophan oxygenase, tryptophan pyrrolase) is considered primarily to be a liver enzyme. However, the same or a very similar enzyme, indoleamine 2,3 dioxygenase is also present in the brain, intestines and other organs. See Gal, E. M. and Sherman, A. D., "L-kynurenine: its synthesis and possible regulatory function in brain", Neurochem. Res. 5:223–239 (1980).

Table 1 depicts several apparent differences between the functions of these enzymes. See Hayaishi, O., "Properties and function of indoleamine 2,3-dioxygenase", J. Biochem 79:13p-21p (1976); Gal, E. M., "Cerebral tryptophan-2,3-dioxygenase (pyrrolase) and its induction in rat brain" J. Neurochem 22:861–863 (1974); and Gal, E. M. and Sherman, A. D., "L-kynurenine: its synthesis and possible regulatory function in brain", Neurochem. Res. 5:223–239 (1980).

TABLE 1

|  | Tryptophan 2,3-dioxygenase | Indoleamine 2,3-dioxygenase |
|---|---|---|
| Similarities |  |  |
| Substrate | L-tryptophan | L-tryptophan |
| Product | N-formyl kynurenine | N-formyl kynurenine |
| Type of protein | heme | heme |
| Inducible by tryptophan | yes | yes |
| Differences |  |  |
| Location | liver | brain and many other organs |
| Type of oxygen used | $O_2$ | $O\text{—}O^-$ |
| Other substrates | none | D-tryptophan 5-hydroxy-tryptophan serotonin melantoin |
| Inducible by cortisol | yes | no |

It is not known whether these differences are due to the presence of the enzyme in a different form in different tissues or to the fact that the enzymes are produced by different genes. For the purposes of this invention, it is unnecessary to determine whether one or two genes is implicated. A reasonable possibility is that the two forms of TO (liver and intestine-brain) represent alternate modes of transcription or mRNA processing of the human TO gene. Unless separately identified, the liver and brain-intestine enzymes are referenced collectively herein as tryptophan oxygenase or TO.

If TO were present only in the liver, then the level of tryptophan in the brain would be almost completely dependent on the blood level of tryptophan and of the compounds that compete for its transport across the blood brain barrier. However, as FIG. 1 shows, tryptophan oxygenase activity is also present in the brain where it is effective to siphon off some of the tryptophan after brain entry and before it is converted to serotonin.

In rats, under normal conditions 70% of the brain tryptophan is converted to serotonin and 30% to brain kynurenine. Gal, E. M. and Sherman, A. D., "L-kynurenine: its synthesis and possible regulatory function in brain", Neurochem. Res. 5:223–239 (1980). Even a moderate increase in brain tryptophan oxygenase could markedly change this ratio and lower the level of brain serotonin. Significant changes in the breakdown of tryptophan in the brain may thus occur concurrently with only moderate changes in the blood tryptophan and serotonin.

In humans, serotonin and tryptophan levels are apparently interdependent, serotonin level abnormalities being a consequence of tryptophan level abnormalities. As FIG. 2 shows, human brain tryptophan can take two major metabolic pathways, i.e., 90% conversion to kynurenine and 10% conversion to serotonin. TO activity is the rate limiting step in the degradation of tryptophan to kynurenine.

Because TO is implicated in both TS and autism, fairly subtle changes in the level of the enzyme would be expected to significantly affect serotonin production. The TO level may be increased in TS and decreased in autism. However, since some autistic children have low levels of serotonin and some TS patients have high levels, the basic defect in both may be a dysregulation (too high or too low) of serotonin.

More particularly, FIG. 3 indicates that the genetic defect in TS related disorders may be either a duplication or a mutation of the TO gene resulting in high levels of hyperinducability, whereas in autism and some forms of MR the TO gene is either defective or deleted.

Since the serotonin levels in some severe mental retardation are even higher than those in autism, it is likely that the genetic defect causing the elevated serotonin is also more severe and may represent a deletion of the TO gene. By contrast, in TS, the TO genes are duplicated or otherwise mutated so the amount of enzyme is increased.

In genetic terms the most detrimental thing that can be done to a gene is to delete it. A single base change mutation within the gene may have no effect, a mild effect or a significant effect on the function of the enzyme that gene makes. Table 2 presents some possible genotypes and phenotypes as a guide to the basic idea. A deletion of a TO gene is termed TO 0, a base pair substitution mutation causing decreased function of TO is termed TO −, a normal gene will be termed TO + and a duplicated gene, or a gene with a mutation causing increased levels or increased efficiency of the tryptophan oxygenase enzyme, is termed TO + +.

TABLE 2

| Type of Defect | Genotype | Effect on Blood Serotonin | Result |
| --- | --- | --- | --- |
| None | TO +/TO + | Normal Levels | Normal |
| Deleted/Deleted | TO 0/TO 0 | Extremely High | Severe M.R. ± Autism |
| Deleted/Mutant | TO 0/TO − | Very High | Autism with M.R. |
| Mutant/Mutant | TO −/TO − | High | Autism Some TS |
| Mutant or Deleted/Normal | TO 0/TO + <br> TO −/TO + | Moderately High | Normal or Mild Autism Some TS |
| Mutant or Dup/Normal Normal | TO ++/TO + | Low Serotonin | TS Some Autism |
| Mutant or Dup/Mutant or Dup | TO ++/TO ++ | Low Serotonin | Homozygous Grade 3 TS Some Autism |

Hence, mutations of the human TO gene which result in decreased activity of the TO gene are likely to be involved in some cases of the autism or autism with mental retardation. These mutations would be various heterozygous or homozygous combinations of deletions or base pair mutations affecting activity or function of the human TO gene or genes.

In contrast, mutations of the human TO gene which result in increased activity, or increased inducability or increased efficiency of the TO gene are likely to be involved in Tourette syndrome and many of the wide range of behaviors associated with the TS spectrum of behaviors. These mutations include various heterozygous or homozygous combinations of gene duplications, or mutations of the regulatory or structural sequences of the human TO gene or genes.

Because the defects are enzyme deficiencies, the autism and MR disorders are autosomal recessive. By contrast, for TS because the enzyme level is apparently increased, the trait is autosomal dominant or semi-dominant.

These examples are meant to be an approximation. An abnormal serotonin level (too high or too low) may cause either autism or TS or autism and TS. Many cases of both occurring in the same patient have been described.

SUMMARY OF THE INVENTION

This invention relates to the diagnosis of genetic Tourette syndrome and related psychiatric and behavioral disorders by genetic tests to identify deletions, duplications or defective alleles in the human tryptophan oxygenase (TO) gene and to probes for use in such tests. More particularly, the invention relates to certain cDNA tryptophan oxygenase clones derived from mRNA and to the use of such clones as probes to identify genomic clones from a human genomic library and to identify the chromosomal location of the human TO gene. The invention also relates to the identification, chromosomal location, isolation, nucleotide sequence and synthesis of the human TO gene and of peptides encoded by the TO gene.

Diagnostic tests are provided for, among other things, Tourette syndrome (TS) chronic motor and vocal tics, attention deficit disorder (ADD) with or without hyperactivity, obsessive-compulsive behavior, unipolar or bipolar affective disorder, phobias, panic attacks, significant premenstrual tension, generalized anxiety disorder, autism, pervasive developmental disorder, dyslexia, learning disabilities, dysgraphia, borderline personality disorder, migraine headaches, exhibitionism, stuttering, delayed speech, schizophreniform disorder, schizoid disorder, drug or alcohol addiction or abuse, bulimia, compulsive eating with obesity, physical or sexual abuse of spouse or children, and severe mental retardation (MR). The fact that TS is a wide-based, generalized behavioral disorder associated with the above list of abnormalities is documented in Comings, D. E. and Comings, B. G., "A controlled study of Tourette syndrome. I. Attention deficient disorder, learning disorders and school problems", Amer. J. Human Genetics 41:701–741 (1987); Comings, D. E. and Comings, B. G., "A controlled study of Tourette syndrome II. Conduct disorder", Amer. J. Human Genetics 41:742–760 (1987); Comings, D. E. and Comings, B. G., "A controlled study of Tourette syndrome. III. Phobias and panic attacks", Amer. J. Human Genetics 41:761–781 (1987); Comings, D. E. and Comings, B. G., "A controlled study of Tourette syndrome IV. Obsessive compulsive and schizoid behavior", Amer. J. Human Genetics 41:782–803 (1987); Comings, D. E. and Comings, B. G., "A controlled study of Tourette syndrome. V. Depression and mania", Amer. J. Human Genetics 41:804–821 (1987); Comings, D. E. and Comings, B. G., "A controlled study of Tourette syndrome. VI. Early development, sleep problems, allergies and handedness", Amer. J. Human Genetics 41:822–838 (1987); Comings, D. E., Tourette Syndrome and Human Behavior, Hope Press, Duarte, Calif. 91009-0188, 830 pages (1990). Hereinafter these abnormalities are collectively referenced as "TS related disorders".

BRIEF DESCRIPTION OF THE FIGURES

FIG. 5 and 5A depict the sequence of the human HTO3 (TDO2) clone and the translation into the open reading frame.

FIG. 6 depicts the sequence of rat pcTO1 and rat TDO2.

FIG. 7 shows the region of homology between the sequences depicted by FIGS. 5 and 5A and FIG. 6.

FIG. 8 depicts the results of hybridization studies to identify the chromosomal location of the human TDO gene.

DETAILED DESCRIPTION OF THE INVENTION

Figure 1:
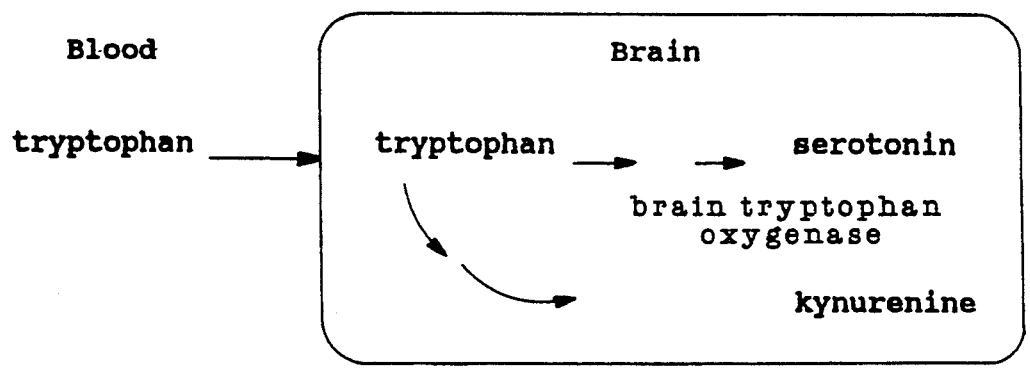
FIG. 1 is a schematic illustration of TDO2-IDO2 activity present in the brain.
Figure 2:
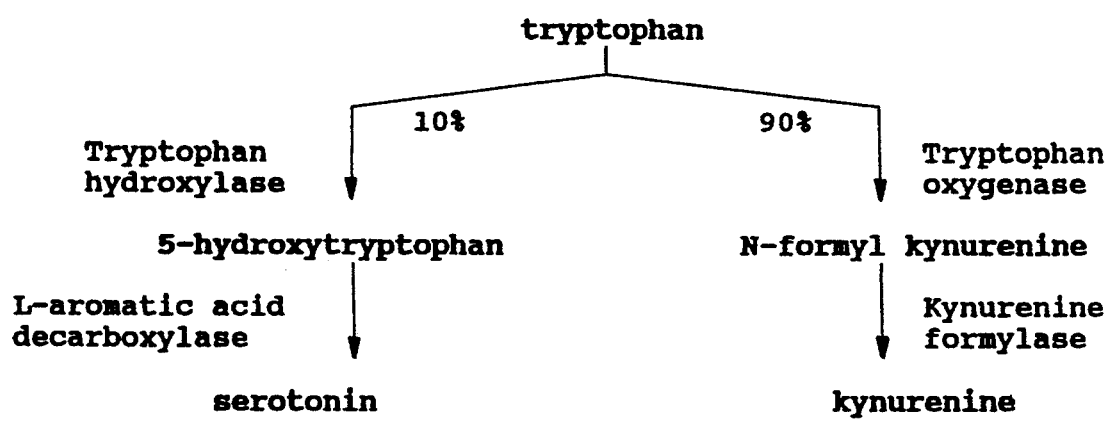
FIG. 2 is a schematic illustration of two metabolic pathways available to peripheral tryptophan.
Figure 3:
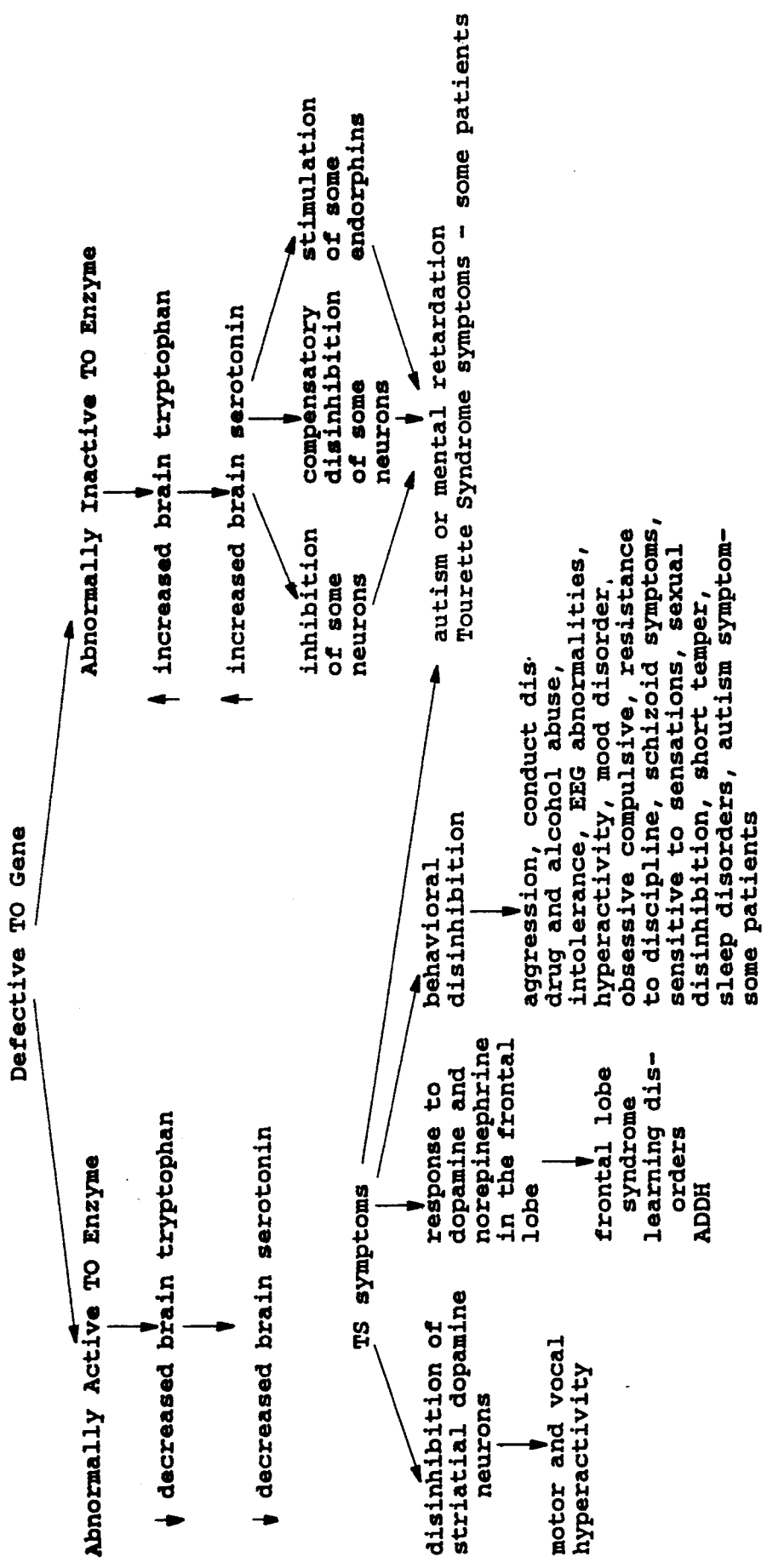
FIG. 3 indicates genetic defects in TDO2-IDO2 that may occur in TS, TS related disorders and autism.

This invention provides genetic tests for TS, autism and the related disorders listed in the "Summary of The Invention". These tests entail the identification of deletions, duplications and other defective alleles of the TO gene.

These genetic tests, per se, may be of conventional nature and involve, for example:

(a) Obtaining DNA from subjects to be tested (blood, skin, hair follicles or any other source).

(b) Identifying mutations in this DNA by hybridization of specific DNA or RNA probes to various parts of the tryptophan oxygenase gene, or DNA surrounding the tryptophan oxygenase gene. The mutations may be partial or complete gene duplications, double or multiple gene duplications, partial or complete gene deletions, single nucleotide substitutions, or frame shift mutations. The probes may, for example, be oligonucleotide probes including allele specific synthetic oligonucleotides, cloned cDNA, genomic DNA fragments, or RNA. The test may include hybridization of DNA electrophoresed in gels, or spotted on a support media, or amplified by DNA polymerases.

The invention includes a cloned cDNA and a genomic DNA probe for the human TO gene useful to conduct such genetic tests. The invention also includes an isolated or synthetic DNA sequence comprising at least a portion of the TO gene sequence, and isolated or synthetic proteins encoded by the TO gene sequence in whole or in part.

Cloning of The Human TO Gene

Schmidt, et al. report the isolation of the rat liver tryptophan oxygenase gene. See *EMBO Journal* 1:1287 (1982). Two cDNA probes, pcTO1 and pcT02 covering parts of the entire rat TO gene are described.

To provide an appropriate human cDNA probe, the rat pcTO1 570 base pair clone was labelled with $^{32}$p and hybridized to a Clonetech human liver cDNA library (Clonetech Laboratories, Inc., Human Liver cDNA, Library Catalogue No. HL 101B, Lot No. 2102).

The Clonetech cDNA library to human liver messenger RNA, in λGT11, was plated on LB plates at a density of 30,000 pfu, using LE192 host *E. coli*. Plaques were lifted in duplicate on BA85 circles, washed in 0.5N NaOH, 1.5M NaCl, then 0.5M Tris, pH 8, 1.5M NaCl, then baked 2 hours at 80° C. The filters were then prehybridized 2 hours in 6× SSC, 1× Denhardts, 100 ug/ml salmon sperm DNA at 65° C., 0.2 ml/sq.cm.

The 565 base pair pcTO1 insert DNA was labelled with $^{32}$P by nick translation and hybridized overnight in 6× SSC, 1× Denhardts, 0.1% SDS, 65° C., then washed in 2× SSC, 1× Denhardts at room temperature for 30 min, then twice in 0.3× SSC, 0.5% SDS, 65° C. for 1 hour. Seventeen of the plaques that were positive on both duplicate plaque lifts were identified and re-plated at low density, about 100 plaques per disk, and final single plaques grown up of each positive clone.

Non-specific artifacts were ruled out if a positive signal (dark spot on the autoradiogram) was obtained in the same position on each duplicate lift as determined by superimposing the two autoradiograms in a slightly shifted position and examination for double spots.

Figure 4:
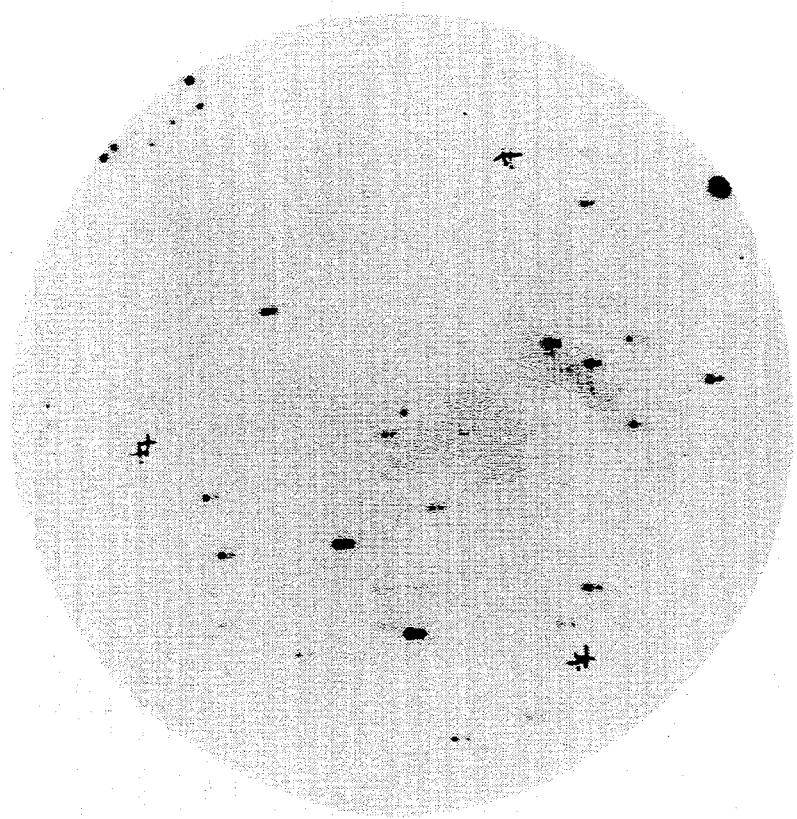
FIG. 4 depicts autoradiograms of duplicate filter lifts from a human liver cDNA library in gtill hybridized with rat liver superimposed and turned slightly to reveal human cDNA clones of human tryptophan oxygenase.

FIG. 4, from just one of nine different dishes, depicts autoradiograms of duplicate filter lifts superimposed and turned slightly. Double spots (duplicate hybridizations) each represent presumptive human cDNA clones of human tryptophan oxygenase. The +'s are orientation markers.

To ascertain if these presumptive clones truly represent human TO, the rat pcTO1 cDNA and one of the human cDNA clones (HTO3) were sequenced, using the Sanger method.

The sequence of human HTO3 clone and the translation into protein to the open reading frame are shown in FIGS. 5 and 5A, the sequence of the rat pcTO1 is shown in FIG. 6, and the region of analogy between the two is shown in FIG. 7. The fact that all 565 base pairs of the rat pcTO1 were 80% homologous with a comparable portion of the human HTO3 sequence and that the protein sequence of the human and the rat cDNA match indicates that the human TO cDNA was isolated. The DNA sequence corresponding to that shown in FIG. 5 or any portion thereof or other regions of the gene and its surrounding DNA sequences may be synthesized in a known manner by commercially available DNA synthesis instruments.

The invention also includes a diagnostic technique for determining the presence or absence of defective human TO genes. Specifically, a probe having a sequence complementary to all or a unique portion of the DNA illustrated by FIG. 5 or to other portions of the TO gene and its surrounding DNA is used to determine the presence or absence of the normal human TO gene in a patient specimen such as a peripheral blood sample. The sequence presented in FIG. 5 represents the 5' end of the transcribed sequences. It is likely that the most important regions for mutations causing an increased level of TO will be in the sequence immediately 5' to this sequence.

Chromosal Location of the Human TO Gene

To identify the location of the human TO gene, DNA from a set of 16 Chinese hamster cell hybrids containing varying amounts of different human chromosomes was obtained from Dr. Mohandas, the Department of Medical Genetics of the University of California at Los Angeles (UCLA). These 16 samples of DNA were cut with a Puv II restriction endonuclease, electrophoresed and Southern blotted on a nylon filter. The DNA restriction fragments were then hybridized with $^{32}$p labelled pHT03. FIG. 8 shows the results. The column labelled A.R. shows the results of the hybridization to the human DNA where ++ to ± indicates positive hybridization and—represents no hybridization. No discrepancies were observed for chromosome #4, thus indicating that the pHTO3 sequences were on chromosome #4.

Figure 9:
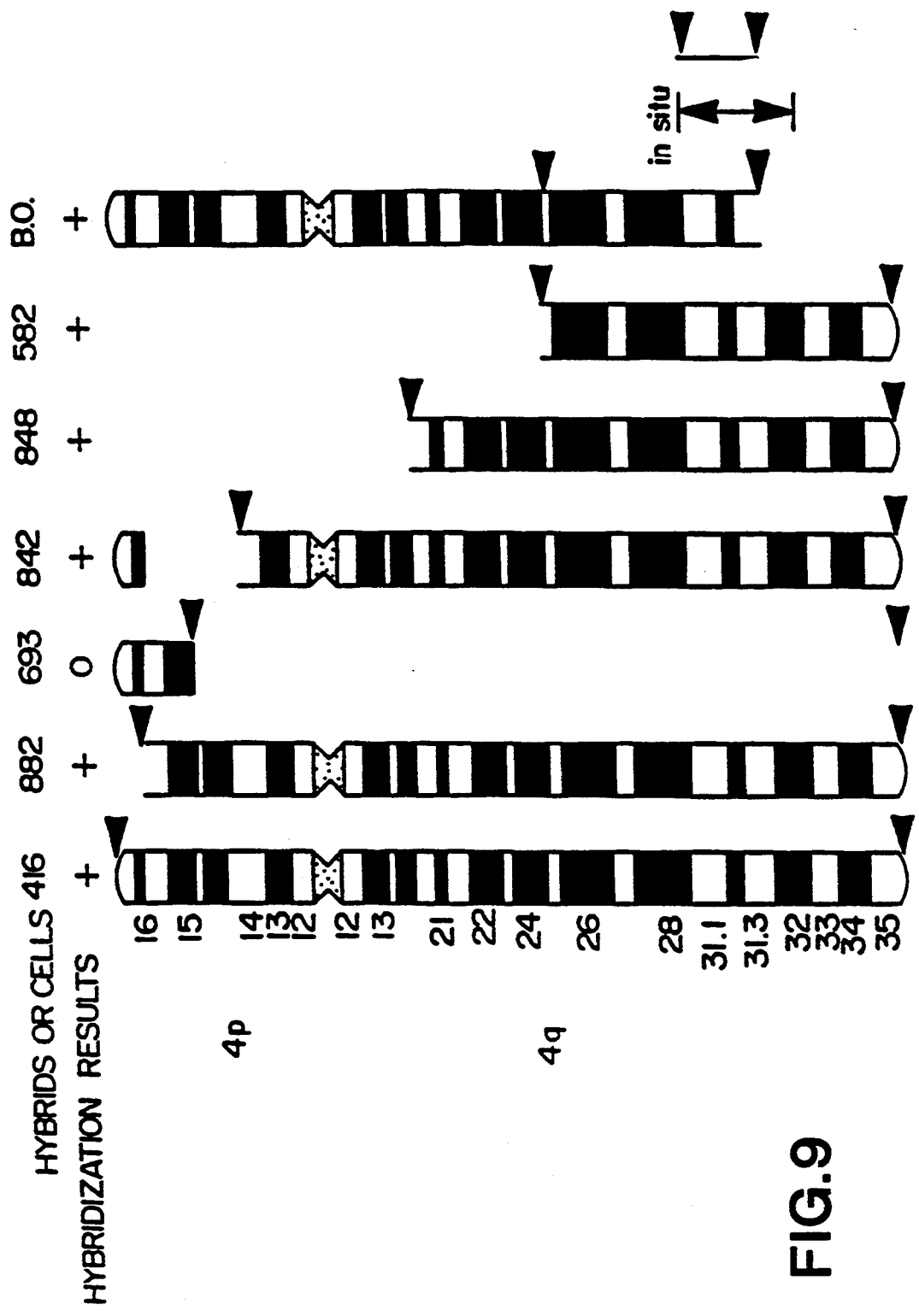
FIG. 9 depicts the chromosomal location of the human tDO2 gene to 4q31.

A different set of DNA from hybrid Chinese hamster cells containing varying amounts of human chromosome #4 was obtained from Dr. John Wasmuth of the University of California at Irvine. A similar series of cutting with the restriction endonuclease Puv II, electrophoresis, Southern blotting and hybridization was performed. The results of the hybridization are depicted by FIG. 9. In the figure, the numbers 416, 582, 693, 842, 848 and 882 indicate hybrids of rodent cells with parts of human chromosome #4 shown. Inasmuch as 693, which contained only the tip of the short arm of chromosome #4 was negative, the gene for pHTO3 was not on this part of the chromosome. Since all the other hybridizations were positive but varying amounts of chromosome #4 were missing from several of these cell hybrids, FIG. 9 shows the gene to pHT03 to be on 4q between band q25 and q31.

To further identify the location of the human TO gene, radioactivity labelled HTO3 was hybridized to human metaphase chromosomes by the technique of in situ hybridization. This indicated the HTO3 gene was on chromosome band 4q 31-32. See FIG. 9.

What is claimed is:

1. An isolated or synthetic DNA comprising the sequence as depicted by FIG. 5.

2. Isolated DNA comprising the human tryptophan oxygenase gene.

3. An oligonucleotide probe having a sequence complementary to the human tryptophan oxygenase gene.

* * * * *